(12) United States Patent
Kelliher et al.

(10) Patent No.: US 7,958,887 B2
(45) Date of Patent: Jun. 14, 2011

(54) NOZZLE PORE CONFIGURATION FOR INTRAPULMONARY DELIVERY OF AEROSOLIZED FORMULATIONS

(75) Inventors: Giles Kelliher, Hayward, CA (US); David Fujimoto, Hayward, CA (US); Justin Drish, Hayward, CA (US)

(73) Assignee: Aradigm Corporation, Hayward, CA (US)

( * ) Notice: Subject to any disclaimer, the term of this patent is extended or adjusted under 35 U.S.C. 154(b) by 745 days.

(21) Appl. No.: 11/683,919

(22) Filed: Mar. 8, 2007

(65) Prior Publication Data

US 2007/0256684 A1 Nov. 8, 2007

Related U.S. Application Data

(60) Provisional application No. 60/781,534, filed on Mar. 10, 2006.

(51) Int. Cl.
*A61M 11/00* (2006.01)

(52) U.S. Cl. .............. 128/200.14; 128/200.24

(58) Field of Classification Search ............. 128/203.15, 128/200.11–200.14, 200.21–200.23; 239/553, 239/391, 520, 556, 560, 561, 566, 596, 102.2, 239/4, 557; 55/418, 419
See application file for complete search history.

(56) References Cited

U.S. PATENT DOCUMENTS

| | | | | |
|---|---|---|---|---|
| 1,587,041 A | * | 6/1926 | Secord | 34/232 |
| 3,812,854 A | | 5/1974 | Michaels et al. | |
| 3,878,992 A | | 4/1975 | MacManus | |
| 4,730,786 A | * | 3/1988 | Nelson | 239/590.3 |
| 4,840,756 A | * | 6/1989 | Ebersole et al. | 264/485 |
| 4,863,647 A | * | 9/1989 | Baylor, Jr. | 264/425 |
| 4,919,810 A | | 4/1990 | Itoh et al. | |
| 5,009,759 A | * | 4/1991 | Serwer et al. | 204/466 |
| 5,079,272 A | * | 1/1992 | Allegrezza et al. | 521/134 |
| 5,152,456 A | * | 10/1992 | Ross et al. | 239/102.2 |
| 5,261,601 A | * | 11/1993 | Ross et al. | 239/102.2 |
| 5,497,763 A | | 3/1996 | Lloyd et al. | |
| 5,497,944 A | | 3/1996 | Weston et al. | |
| 5,544,646 A | | 8/1996 | Lloyd et al. | |
| 5,590,383 A | * | 12/1996 | Sekhar et al. | 419/2 |
| 5,660,166 A | | 8/1997 | Lloyd et al. | |
| 5,709,202 A | | 1/1998 | Lloyd et al. | |
| 5,718,222 A | | 2/1998 | Lloyd et al. | |
| 5,758,637 A | | 6/1998 | Ivri et al. | |
| 5,823,178 A | | 10/1998 | Lloyd et al. | |
| 5,829,435 A | | 11/1998 | Rubsamen et al. | |
| 5,906,202 A | | 5/1999 | Schuster et al. | |
| 5,952,605 A | * | 9/1999 | Sievers et al. | 136/205 |
| 6,295,986 B1 | | 10/2001 | Patel et al. | |
| 6,689,986 B2 | | 2/2004 | Patel et al. | |

(Continued)

*Primary Examiner* — Justine R Yu
*Assistant Examiner* — Kevin Chu
(74) *Attorney, Agent, or Firm* — Karl Bozicevic; Bozicevic, Field & Francis LLP (57) ABSTRACT

The present invention describes the configuration of a porous sheet for improving the efficiency for generating an aerosol from a liquid formulation. This aerosolized liquid formulation can be used for intrapulmonary delivery of pharmaceutically active drugs and diagnostic agents when said invention is used in conjunction with the appropriate device. The individual pores in each array (defined as the rows and columns of pores for example in a rectangular array) are generated such that there is a discrete or continuous variation in the pore size within the plurality of pores on the sheet. The drug is subsequently aerosolized by forcing the liquid formulation through the pores on the sheet. The resulting aerosol will contain a controlled range of particle sizes defined by the properties of the porous sheet and the liquid formulation.

10 Claims, 8 Drawing Sheets

U.S. PATENT DOCUMENTS

| | | | |
|---|---|---|---|
| 6,732,943 B2 | 5/2004 | Srinivasan | |
| 6,764,023 B2 * | 7/2004 | Peng et al. | 239/101 |
| 6,827,287 B2 * | 12/2004 | Elrod et al. | 239/102.1 |
| 6,904,945 B2 * | 6/2005 | Boillat et al. | 141/130 |
| 6,926,208 B2 * | 8/2005 | Ivri | 239/4 |
| 7,195,179 B2 * | 3/2007 | Miller et al. | 239/302 |
| 7,229,028 B2 * | 6/2007 | Chen et al. | 239/102.2 |
| 2002/0005442 A1 * | 1/2002 | Watanabe et al. | 239/596 |
| 2002/0134373 A1 * | 9/2002 | Gonda | 128/200.14 |
| 2002/0175220 A1 * | 11/2002 | Pence | 239/102.2 |
| 2003/0192959 A1 * | 10/2003 | Hess et al. | 239/69 |
| 2004/0021006 A1 * | 2/2004 | Mounteney | 239/398 |
| 2004/0050953 A1 * | 3/2004 | Terada et al. | 239/102.2 |
| 2005/0121537 A1 * | 6/2005 | Ellson et al. | 239/102.2 |
| 2006/0219806 A1 * | 10/2006 | Wang et al. | 239/102.2 |
| 2006/0237563 A1 * | 10/2006 | Hupp | 239/556 |

* cited by examiner

NOZZLE PORE CONFIGURATION FOR INTRAPULMONARY DELIVERY OF AEROSOLIZED FORMULATIONS

CROSS-REFERENCE

This application claims the benefit of U.S. Provisional Application No. 60/781,534, filed Mar. 10, 2006, which application is incorporated herein by reference.

FIELD OF THE INVENTION

The invention relates to a modified array of pores in thin sheets of materials that can subsequently be used in the creation of aerosols with improved aerosol generation efficiency when used with liquid formulations. More specifically, it deals with arrays of pores in thin sheets of material that can be used as nozzles in a drug delivery device. The nozzles are characterized by controlled variations in the exit diameters of the pores.

BACKGROUND OF THE INVENTION

In a number of applications, a sheet having a plurality of regularly or irregularly spaced pores therein is utilized. For example, such a porous sheet might be utilized as a component in the manufacture of filters, ink jet printer cartridges or fuel injectors. Alternatively, such a porous sheet could be used for generating an aerosol, spray or mist that could be used in the delivery of pharmaceutically active drugs or diagnostic agents.

The pharmaceutically active drug or diagnostic agent could be delivered in a variety of different ways, including but not limited to nasal, oral, topical, dermal, vaginal, intra-tracheal instillation, or ocular. In the preferred embodiment of this invention, a pharmaceutically active drug or diagnostic agent can be delivered inside the human body through the inhalation of an aerosol, spray or mist of said drug or agent generated using an intrapulmonary delivery system. One component of this intrapulmonary delivery system is the sheet containing a plurality of pores. For the purposes of liquid formulations, the aerosol is produced by energizing the liquid formulation, causing the liquid formulation to pass through the sheet containing a plurality of nozzle pores (the array). The attributes of this porous sheet will facilitate the desired control over the particle size distribution (PSD) and emitted dose (ED) of the aerosol treated for inhalation into a subject's lungs. Some existing intrapulmonary delivery devices also provide mechanisms to control the amount of drug delivered to the patient. Examples of the existing intrapulmonary drug delivery devices include Metered Dose Inhalers (MDIs), Dry Powder Inhalers (DPIs) and Nebulizers.

Intrapulmonary delivery of pharmaceutically active drugs or diagnostic agents to the respiratory tract generally requires that the aerosolized particles have a diameter of 12 microns or less. Depending on the intended usage; topical or systemic, the optimal range of particle size distribution can vary. Thus, for topical applications the generally accepted range for an aerosolized particle is in the range of 1.0 to 12.0 microns, preferably 2 to 6 microns. For systemic delivery applications, this range in generally in the 0.25 to 6.0 micron range, preferably 0.5-4 microns, more preferably 1-3.5 microns.

U.S. Pat. Nos. 5,544,646; 5,709,202; 5,497,763; 5,7182,222; 5,660,166; 5,823,178; 5,829,435; 5,906,202, 5,497,944; 5,758,637; and 3,812,854 describe devices and methods useful in the generation of aerosols suitable for drug delivery. These devices generate fine, uniform aerosols by passing a formulation through a porous sheet that can be created, for example, by laser ablation. Examples of available devices that use similar methods of aerosol generation include but are not limited the Pari E-flow®, Aerogen Aeroneb®, Omron Microair®, Boehringer-Ingelheim Respimat®, the Medspray® aerosol device, and the Aradigm AERx® system.

In the systems and methods cited above, the emitted dose of the liquid formulation or measure of aerosolization efficiency is affected by a number of variables including the characteristics of the porous sheet. Utilizing embodiments of this invention facilitates an additional degree of control over the efficiency of aerosol generation and drug delivery.

Previously, the advantages of having all pore sizes the same has been stressed. For example, in U.S. Pat. No. 3,812,854, "in the preferred embodiment of this invention, wherein aerosols for inhalation therapy are produced, it is most often preferred to have uniform particle sizes. Bodies having uniform pore diameters in the range of from 0.5 to 5 microns produce aerosols ideal for many inhalation applications."

Controlling the aerosolization efficiency, or amount of formulation emitted through the characteristics deliberately introduced to the porous sheet as described in this invention can potentially improve the utilization and delivery of a pharmaceutically active drug or diagnostic agent to the intended target within the respiratory tract. A modified porous sheet of the invention can potentially lead to a reduction in the cost of the liquid formulation container utilizing this porous sheet and reduce, thereby, the cost of treatment for a patient.

SUMMARY OF THE INVENTION

Groups of pores in sheets of material that exhibit deliberate gradation or discrete step changes in the pore sizes contained with the group are provided. The inclusion of the gradient or discrete step changes in pore sizes is accomplished during the formation of the pores in the sheets and leads to improved efficiency when generating aerosols, mists or sprays through these porous sheets.

Methods for generating pores in thin sheets of material, ranging from thin polymer films, medical grade metals, glass or ceramic have been previously developed and described. U.S. Pat. No. 6,732,943 describes such methods that are used to form pores that uniformly penetrate the sheet material in use. In summary, these methods typically utilize the energy of a laser source directed onto the sheet so as to form pores through the sheet. The pores can be formed either individually or in plurality with a single or multiple groupings of arrays of pores on the sheet. The laser source may be controlled using a mask and/or beam-splitting and/or focusing techniques.

In one aspect of the invention, a solid-state laser, (e.g. a neodymium doped yttrium aluminum garnet (Nd:YAG) laser) is used as the laser source.

In another aspect of the invention, an excimer laser is used as the laser source.

An advantage of the method of invention is that the pore configuration form in the sheet can lead to measurable improvement in the efficiency of aerosol generation or emitted dose of a liquid formulation used in conjunction with a device for intrapulmonary delivery of pharmaceutically active drugs or diagnostic agents.

Another aspect of the invention is to provide a nozzle, comprising: a sheet of material with a plurality of pores in the sheet, wherein the pores are grouped in a plurality of groups and each group is comprised of a plurality of pores of substantially the same size within a given group and further wherein the pore size within different groups change in a direction from a first side of the sheet to a second side of the sheet.

In other aspects of the nozzle may be configured wherein pore diameter between pores of one group to another group differs by 5% or more or wherein pore diameter between pores of one group to another group differs by 10% or more or wherein pore diameter between pores of one group to another group differs by 20% or more or wherein the groups of pores are in rows and different rows have gradually different pore sizes between rows from the first side of the sheet to the second side of the sheet.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Before the present nozzle configurations, devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a pore" includes a plurality of such pores and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "array" or "nozzle array" or "pore array" and the like as used herein, refers to a collection or plurality of pores as may be included in a sheet such as a sheet of flexible polymeric material. This collection of pores can be described geometrically in either rectangular or circular coordinates or any other coordinate system, or be randomly distributed.

The term "array" will be used hereinafter to describe a grouping, collection and/or plurality of pores that could be arranged in a variety of geometric configurations. For example, an array could be a plurality of pores arranged in as a rectangular array with rows and columns or a radially configured array. In this embodiment of the invention, the array would contain a continuous or discrete gradient (variation) in the size of the pores. Various embodiments of the invention have been described hereinafter.

The terms "porous sheet" and "porous film", used interchangeably herein, refer to a sheet of material having any given outer parameter shape, but preferably having a convex shape, wherein the sheet has a pore array therein, i.e. plurality of pores therein, which pores or openings may be placed in a regular or irregular pattern, and which pores have an unflexed diameter of their exit aperture in the range of 0.25 micron to 50 microns and a pore density in the range of 1 to 1,000 pores per square millimeter. The porous sheet has a porosity of about 0.0005% to 10%, preferably about 0.01% to 2%, more preferable about 0.01% to 0.1%. In one embodiment, the porous sheet comprises a single row of pores on, e.g., a large piece of sheet material. The pores may be planar with respect to the surface of the porous sheet material, or may have a conical configuration. The sheet may be a polymer film, a metal, a glass, a ceramic or any other pharmaceutically suitable engineering material.

The term "complete pore", as used herein, refers to a pore, which extends through the entire thickness of a film, i.e., the pore opens onto both surfaces (i.e., entrance surface, to which the liquid formulation is applied under pressure, and exit surface, from which the liquid formulation is extruded) of the film or sheet.

The term "chemical emitted dose", "emitted dose" and "delivered dose", as used herein, refers to an amount of pharmaceutically active drug or diagnostic agent delivered to a patient from an aerosol generated from a formulation. The aerosol created as a result of being moved through a porous sheet of the invention will exhibit a characteristic particle size distribution that is the result of the liquid formulation and the porous sheet, among other factors.

The term "gradient", as used herein, refers to a variation in the individual pore size within the plurality of pores formed on the sheet. This gradient could take on the form of being either a continuous or discrete change in the pore size within the plurality of pores. The gradient can also have the characteristic of being a negative or positive gradient; wherein, the negative gradient represents a decreasing pore size with respect to the direction of the airflow across the porous sheet or in the case of a positive gradient having an increasing pore size with respect to the direction of the airflow across the porous sheet. Although it is preferred that the gradient be a linear gradient, i.e. a continuous change across the sheet, any gradient may be used, including a discrete change, a parabolic profile, or any other profile.

The terms "incomplete pore" and "partial pore", are used interchangeably herein, to refer to a pore, which does not open onto both surfaces of the thin film. A pore has an entrance aperture to which a flowable substance is applied under pressure, and an exit aperture, from which flowable substance is extruded.

The term "substantially through" with reference to the pores being formed in the sheet or material shall mean pores which either completely traverse the width of the sheet or are formed to have a thin peelable layer over their exit aperture. The pores formed with a peelable layer over their exit apertures are formed so as to peel outward at a substantially lower pressure than would be required to rupture the sheet in the nonporous areas.

The term "jet" is used herein to describe the column of liquid or stream of formulation that exits each pore under pressure as the liquid formulation is extruded through the porous sheet. The jet or stream completely separates from the porous sheet and disassociates into particles forming an aerosol.

The term "ooze" is used herein to describe the amount of liquid formulation that exits the pore as liquid as opposed to being a jet or an aerosol, mist or spray. The ooze can remain in contact with the porous sheet until it is wiped away.

The term "porosity" is used herein to refer to a percentage of an area of a surface area that is composed of open space, e.g., a pore, hole, channel or other opening, in a film, sheet, nozzle, filter or other material. The percent porosity is thus defined as the total area of open space divided by the area of the material, expressed as a percentage (multiplied by 100). The "area of the material" is the area which has pores in it and not a surrounding poreless border area, if any. High porosity (e.g., a porosity greater than 50%) is associated with high flow rates per unit area and low flow resistance. In general, the porosity of the nozzle is less than 10%, and can vary from $10^{-3}\%$ to 10%, while the porosity of the filter is at least 1%, and preferably it is at least 50% or more porous.

The terms "package" and "disposable package" and the like are used interchangeably herein and refer to a container or two or more containers linked together by an interconnecting means wherein each container preferably includes one or more channels which provide for fluid connection from the container to a nozzle comprised of a porous sheet, which nozzle is preferably not positioned directly over the container, and wherein each container includes at least one surface that is collapsible in a manner so as to allow the forced displacement of the contents of the container and out the nozzle (without rupturing the container) in a manner such that the contents are either aerosolized or ooze out onto the porous membrane. There are at least two variations of the package, depending on whether the drug can be stably stored in a liquid form or must be stored dry and combined with liquid immediately prior to aerosolization.

The contents of each container preferably comprises a formulation, preferably a flowable formulation, more preferably a liquid, flowable formulation, which comprises a pharmaceutically active drug or a diagnostic agent. If the drug or diagnostic agent is not liquid and of a sufficiently low viscosity to allow the drug to be aerosolized, the drug or diagnostic agent is dissolved or dispersed in an excipient carrier, preferably without any additional material such as preservatives that might affect the patient. When the contents must be stored in a dry state, the package further includes another container that holds the liquid and can be combined with the dry drug immediately prior to administration.

The term "container" is used herein to refer to a receptacle for holding and/or storing a drug formulation. The container can be single-dose or multidose, and/or disposable or refillable. The container may be refillable or a single use disposable container.

The terms "aerosol" and "aerosolized formulation," and the like, are used interchangeably herein to refer to a volume of air which has suspended within it particles of a formulation comprising a drug or diagnostic agent wherein the particles have a diameter in the range of 0.5 to 12 microns, for respiratory therapy, or in the range of 15 to 50 microns for ocular therapy, or in the range of 2 to 30 microns, preferably 10 to 20 microns, for nasal delivery.

The terms "formulation" and "flowable formulation" and the like are used interchangeably herein to refer to any pharmaceutically active drug (e.g., a respiratory drug, or drug that acts locally or systemically, and that is suitable for respiratory delivery) or diagnostic agent combined with a pharmaceutically acceptable carrier in flowable form having properties such that it can be aerosolized to particles having a diameter of 0.5 to 12.0 microns for respiratory therapy, or 15 to 75 microns for ocular therapy. Such formulations are preferably solutions, e.g., aqueous solutions, ethanolic solutions, aqueous/ethanolic solutions, colloidal suspensions and microcrystalline suspensions. Preferred formulations are drug(s) and/or diagnostic agent(s) dissolved in a liquid, preferably in water.

The terms "individual", "subject", or "patient", used interchangeably herein, refers to an animal, preferably a mammal, generally a human. The patient may be under the care of a doctor or simply be a subject treated for a disease.

Invention Embodiments

The present invention describes a configuration for a porous sheet used to create an aerosol, mist or spray for the delivery of a pharmaceutically active drug or diagnostic agent to a patient when used in conjunction with an intrapulmonary delivery device. This porous sheet as described by this invention, provides better efficiency in the generation of an aerosol, mist or spray that is effectively delivered to the patient, as compared to the existing methods and systems. The improved aerosol generation efficiency is realized by using a liquid formulation container with an integral porous sheet containing plurality of pores exhibiting an intentional continuous gradation or discrete change in pore size as shown in the arrays of any of FIG. 2, FIG. 3 and FIG. 4.

Figure 1:
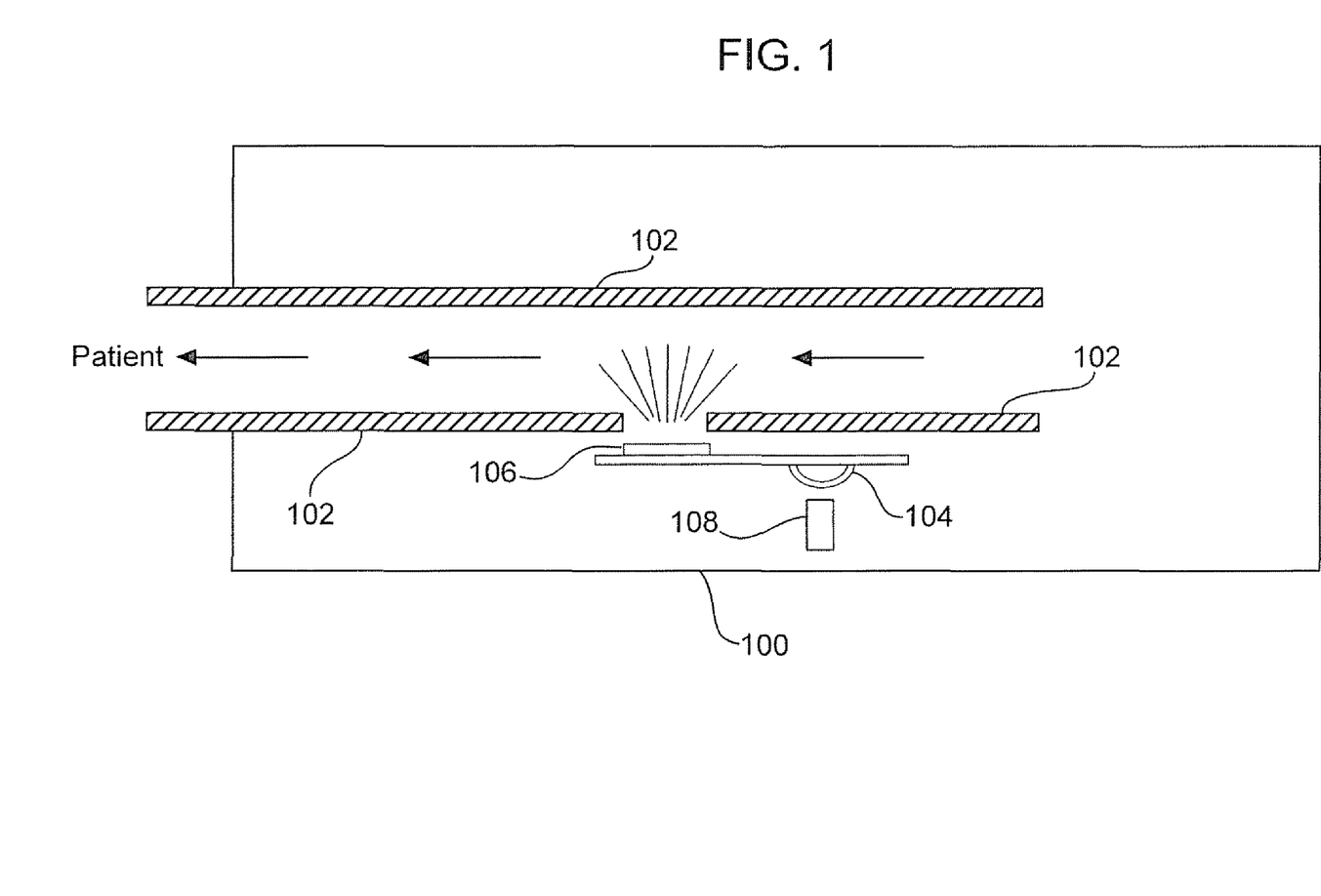
FIG. 1 is a schematic diagram representing a drug delivery device for intrapulmonary delivery of drugs, in accordance with one embodiment of the invention.

FIG. 1 is a schematic diagram representing a pulmonary drug delivery device for intrapulmonary delivery of pharmaceutically active drugs and diagnostic agents, in accordance with one embodiment of the invention. A drug delivery device 100 includes an airway 102, a liquid formulation container 104 with a porous sheet or membrane 106 and a pressure-applying module 108. The porous sheet 106 has two or more pores on one surface of the sheet. Each plurality of pores is defined by a geometric array with rectangular or circular coordinates.

Figure 2:
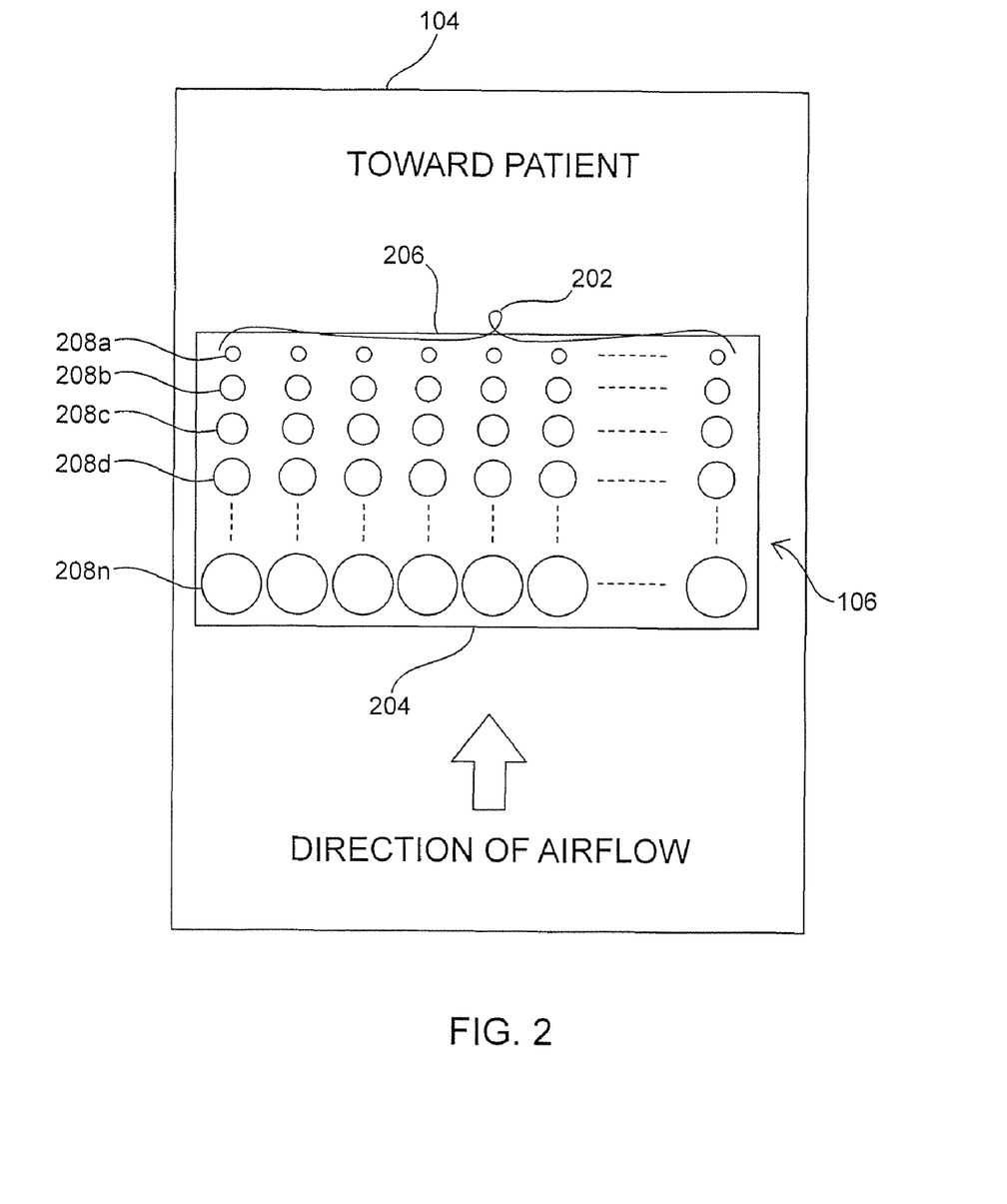
FIG. 2 is a schematic diagram of a top view of a porous sheet with continuous gradient used in conjunction with a drug delivery device, in accordance with one embodiment of the invention.
Figure 3:
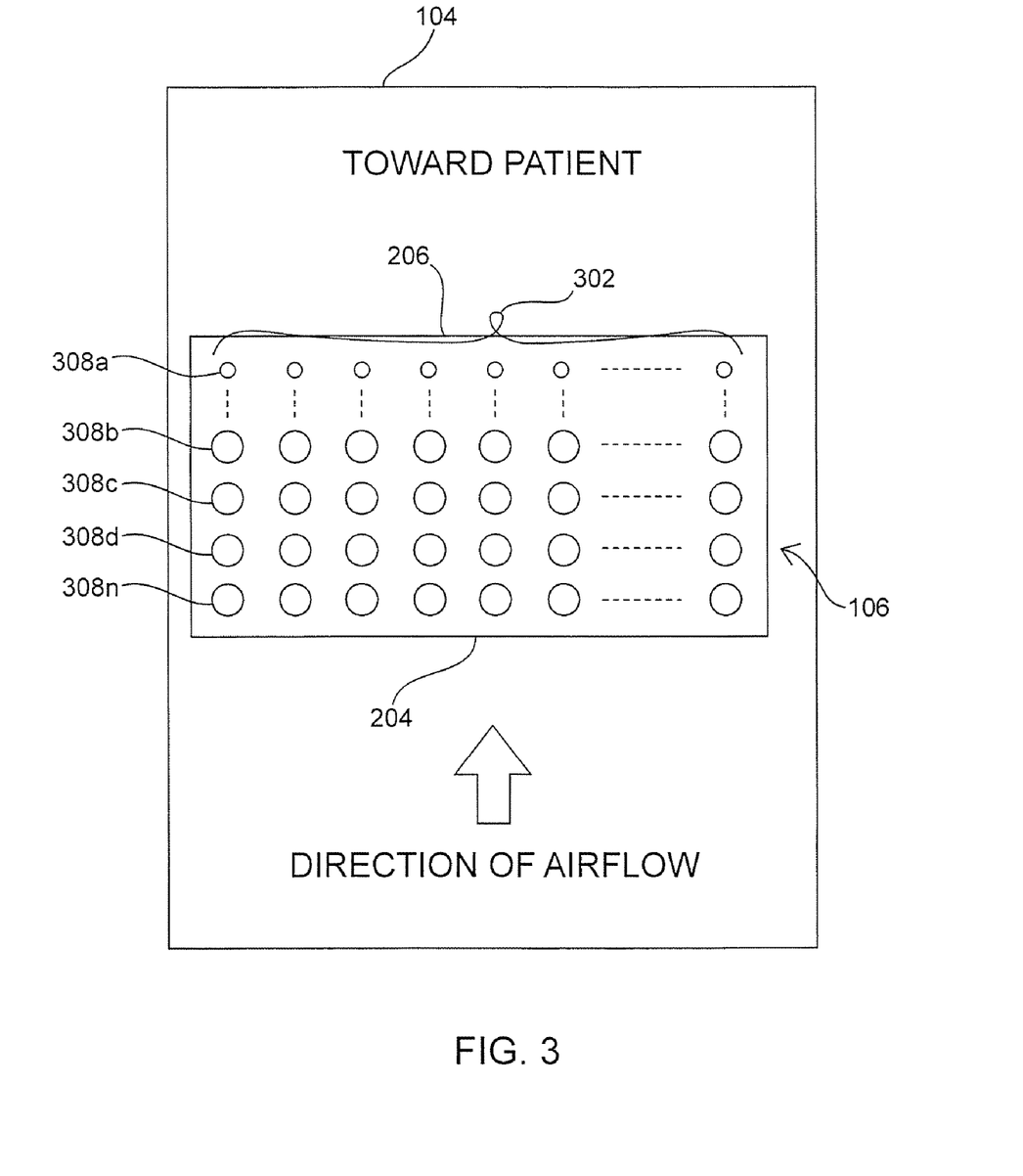
FIG. 3 is a schematic diagram of a top view of a porous sheet with a discrete section of negative gradient.
Figure 4:
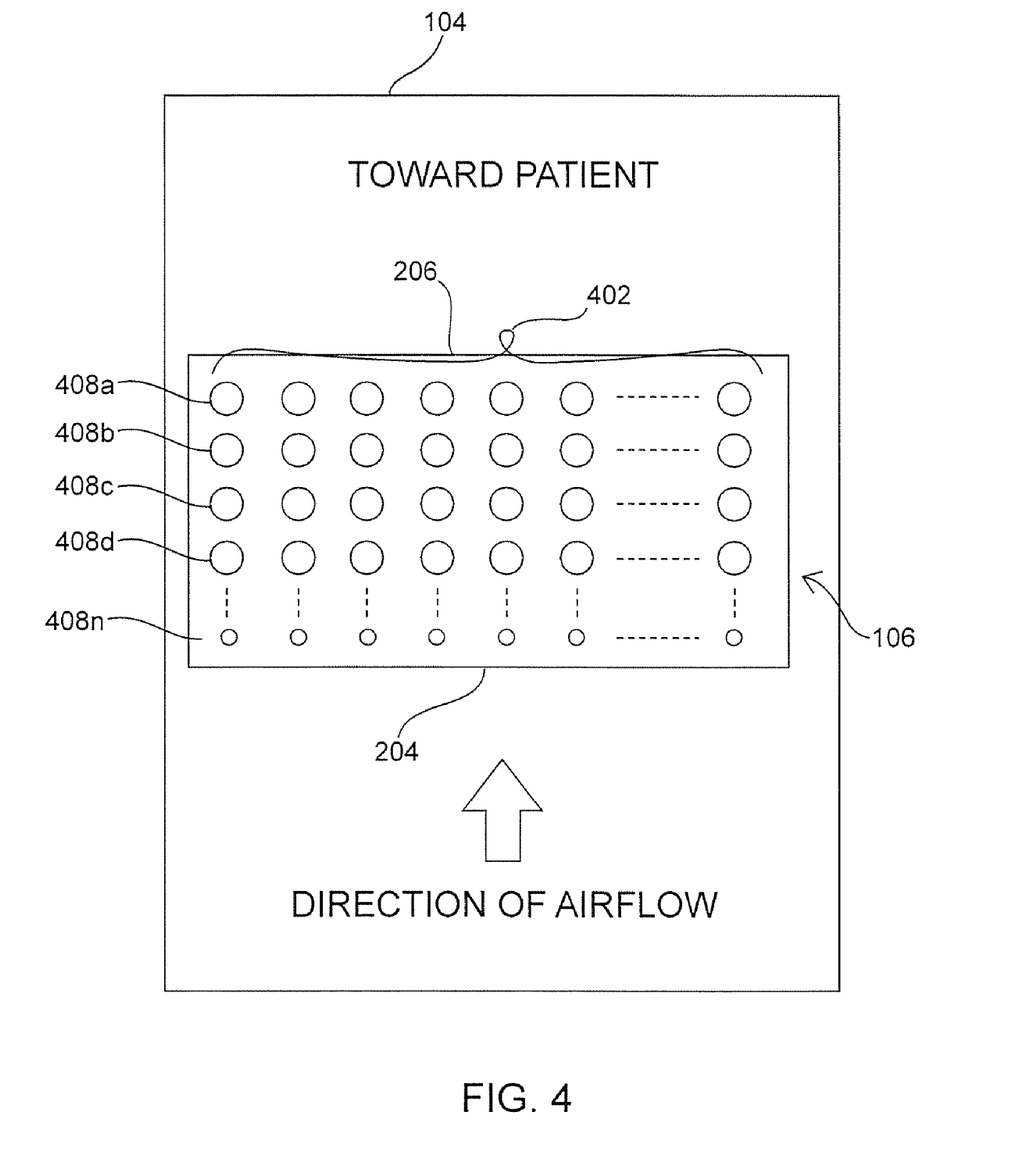
FIG. 4 is a schematic diagram of a top view of a porous sheet with a discrete section of positive gradient.

Different examples of arrangements of pores is schematically shown in conjunction with FIG. 2, FIG. 3 and FIG. 4. A liquid formulation is to be delivered to the user in the form of a spray, mist or aerosol by pressurizing said formulation and causing it to flow through the pores of the porous sheet 106 that is integrated with the liquid formulation container 104 to form an aerosol. A user inhales the aerosolized drug with the help of airway 102.

The liquid formulation is a flowable formulation with a relatively low viscosity that can be easily aerosolized, e.g. an aqueous and/or alcohol solution. In accordance with one embodiment of the invention, the pharmaceutical ingredient is dissolved or dispersed in a carrier in order to decrease the viscosity of the liquid formulation. Examples of liquid formulations include, but are not limited to, ethanoic solutions, aqueous solutions, and colloidal suspensions. The viscosity of the liquid formulation is maintained in order to facilitate aerosolization of the liquid formulation.

In one embodiment of the invention, the liquid formulation is a pharmaceutically active drug of any type dissolved in a carrier. Examples of a pharmaceutically active drug include respiratory drugs, systematically effective drugs (e.g. insulin or nicotine) and the like. Further, the pharmaceutically active drug also includes new drug entities to be developed in future that can be administered by the intrapulmonary route. In a preferred embodiment of the invention, the pharmaceutically active drug comprises insulin or analogs of insulin, for example monomeric insulin. Further, the insulin formulation may be with or without any excipients.

On application of pressure the liquid formulation contained in the liquid formulation container is converted to aerosolized form. Pressure applying module (e.g. a cam, piston or gas pressure) 108 generates the required pressure so that the liquid formulation is dispensed through the porous sheet 106 that is integrated to the liquid formulation container 104 resulting in the generation of an aerosol, spray or mist. In one embodiment of the invention, pressure-applying module is a piston coupled to a servo driven motor assembly. In another embodiment, the pressure applying module is a piston coupled to a spring. When the liquid formulation container 104 with the integral porous sheet 106 is inserted into the device, there is no pressure applied to the liquid formulation container 104. When the device is activated, the servo motor drives the piston to a position determined by the amount of dosing required, in turn exerting pressure on the liquid formulation container 104 forcing the liquid formulation through the porous sheet 106. The liquid formulation coming out of the nozzles forms streams or jets which are unstable. The streams break up into droplets due to surface tension. The size of the droplets is affected by factors such as the size of the pores on the sheet, temperature of the air surrounding the liquid formulation, and solids content of the liquid formulation. In an embodiment of the invention, the size of the droplets is in the range of about 0.5 microns to 12 microns.

In another embodiment of the invention, pressure-applying module 108 is substituted with or supplemented with a vibrating device. This vibration could be applied to the porous sheet, or to the formulation, to facilitate and control the formation of individual droplets, which comprise the aerosol, spray or mist. The frequency of vibrations can be varied depending upon the size of the pores and the viscosity of the liquid formulation, as well as the desired target size range and aerosol generation rate for the resulting aerosol, mist or spray.

FIG. 2, FIG. 3 and FIG. 4 provide schematic top views of a porous sheet 106 that would be integrated with the liquid formulation container 104, in accordance with an embodiment of the invention. Liquid formulation container 104 may be a rectangular liquid formulation container. In one embodiment of the invention, the porous sheet consists of a collection of several hundred individual pores arranged in a rectangular array. The array may contain 5 to 5000 pores, preferably 100 to 1000 pores, more preferably 300 to 600 pores. According to an embodiment of the invention, the porous sheet 106 consists of an array of 448 pores arranged in seven (7) rows and sixty-four (64) columns. The dimensions of this array of pores is approximately 3 mm long and 0.3 mm wide. The pores are conical in shape, having the wide end towards pressure applying module 108 (see FIG. 7) and narrow end at the outer edge from which the liquid formulation is dispensed resulting in the generation of an aerosol. The ratio of the entrance to exit diameter of the pores is greater than 4, preferably greater than 10, more preferably greater than 20. However, the ratio may be different for different rows or pores gradually changing from one row to the next.

Liquid formulation container 104 has an integrated porous sheet 106, with a defined array of pores therein. Although only a single array of pores has been illustrated in FIG. 2, FIG. 3 and FIG. 4, it will be apparent to those skilled in the art that this porous sheet 106 can have more than one array of pores, i.e. a plurality of arrays on each nozzle.

In FIG. 2, is a representation of an array 202 of pores on a sheet, with the individual circles defining the various pores on the sheet 106, through which a liquid formulation could be extruded. In this example, the pores exhibit a continuous gradation in pore size with the pores being arranged in the form of a rectangular array.

In FIG. 2, row 208a, row 208b, row 208c, row 208d and row 208n represent the various rows of this rectangular array, where "n" can be any integer value. In this example with a continuous gradient, the difference between the average diameters of the pores of two adjacent rows is the same throughout the array. Thus, the difference between the diameters of the pores of the row 208b and a row 208c is equal to the difference between the diameters of the pores of the row 208a and the row 208b. Side 204 and side 206 refer to the two sides of porous sheet with respect to the directionality of airflow. Side 204 is the side away from the patient and side 206 is towards the patient. Thus, when the user patient inhales the liquid formulation; air passes over liquid formulation container 104 in a direction from side 204 towards side 206. The array is created so that the pore size of each row gets smaller with rows closer to the patient.

In another embodiment of the invention, FIG. 3 illustrates an example of an array 302 that exhibits a negative gradient with a discrete step change in the average pore size as opposed the continuous gradation presented in FIG. 2. In the example of the discrete step change, the gradient can be non-uniform, i.e., the difference between the diameters of the pores within adjacent rows is not same throughout the array. The difference between the diameters of the pores of the row 308a and the row 308b is not equal to the difference between the diameters of the pores of the row 308b and the row 308c. In this example, the row 308a exhibits a smaller average pore size in the row closest to the patient, with the remainder of the rows (e.g. 308b) containing a monodisperse population of pore sizes that is larger than that contained in row 308a.

In another embodiment of the invention, FIG. 4 illustrates an example of an array 402 that exhibits a positive gradient with a discrete step change in the average pore size as opposed the continuous gradation presented in FIG. 2. In this example, the row of pores away from the user or the $n^{th}$ row, row 408n exhibits a smaller average pore size, with the remainder of the rows (e.g. 408d) containing a monodisperse population of pore sizes that is larger than that contained in row 408n.

Although only porous sheets configured as rectangular arrays have been illustrated in FIG. 2, FIG. 3 and FIG. 4, it will be apparent to those skilled in the art that arrays with other configurations, such as circular arrays, triangular arrays or other geometries with radial coordinates could be configured in a similar fashion. Furthermore, it will be apparent to those skilled in the art that arrays exhibiting one or more rows with a discrete step change in pore size could be constructed.

The gradient is defined as the average difference between the sizes of pores of different rows, or the rate of change of the holes as the array is traversed. In one embodiment of the invention, the gradient is the difference between the average diameters of the pores of the row closest to the patient relative to the row furthest away from the patient within a single array of pores. For example, the gradient for the array 202 illustrated in FIG. 2 is calculated by taking the difference between the diameters of the pores of row 208a and row 208n. If the resulting difference is positive then the gradient is referred to as a positive gradient, and if the difference is negative then the gradient is referred to as a negative gradient, as illustrated in FIG. 4 and FIG. 3 respectively.

The inclusion of specific amounts of gradient, either continuous or discrete steps of gradation into the array configuration of pores on a sheet has been shown to improve the efficiency of aerosol generation and in turn improvements to the delivered amount of a pharmaceutically active drug.

Figure 5:
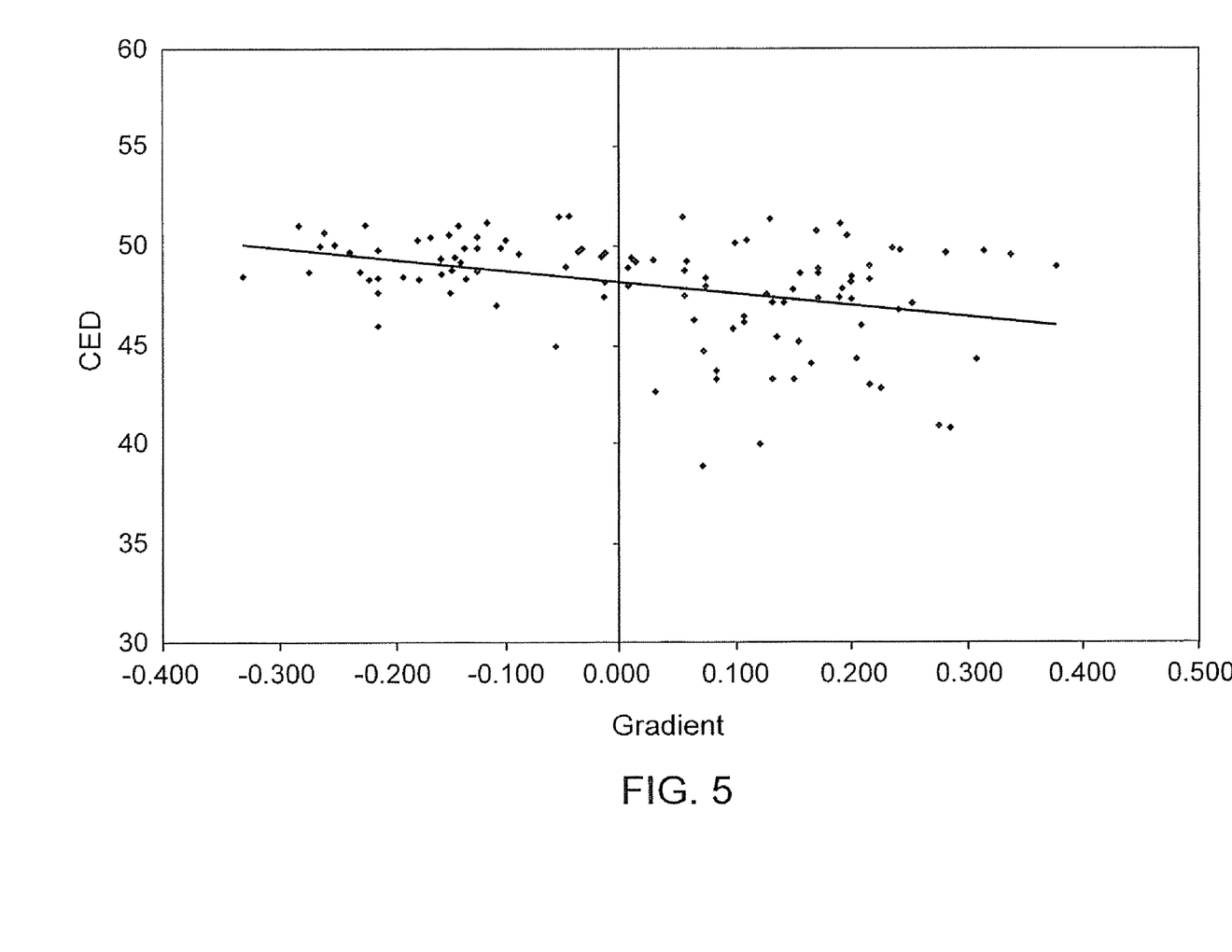
FIG. 5 is a graph that illustrates the effect of gradient on amount of chemical emitted dose (CED).

FIG. 5 is a graph that illustrates the effect of gradient on the amount of Chemical Emitted Dose (CED). CED is plotted on Y-axis and gradient in the size of pores on the liquid formulation container is plotted on X-axis. The CED represents an in vitro measure of the amount of a pharmaceutically active drug or diagnostic agent that is effectively delivered from the device to the patient. This assay is designed to be used as a surrogate for determining the bioavailability of a pharmaceutically active drug in-vitro. From FIG. 5, the mean value for Chemical Emitted Dose is higher in the case of the porous sheet exhibiting a negative gradation in the average pore size on the sheet versus that with a positive gradation of pore size. Also of note is the fact that the variance or standard deviation of the resulting mean value for CED is substantially improved when the porous sheet exhibits a negative gradation in the average pore size in comparison to that featuring a positive gradation in pore size.

Figure 6:
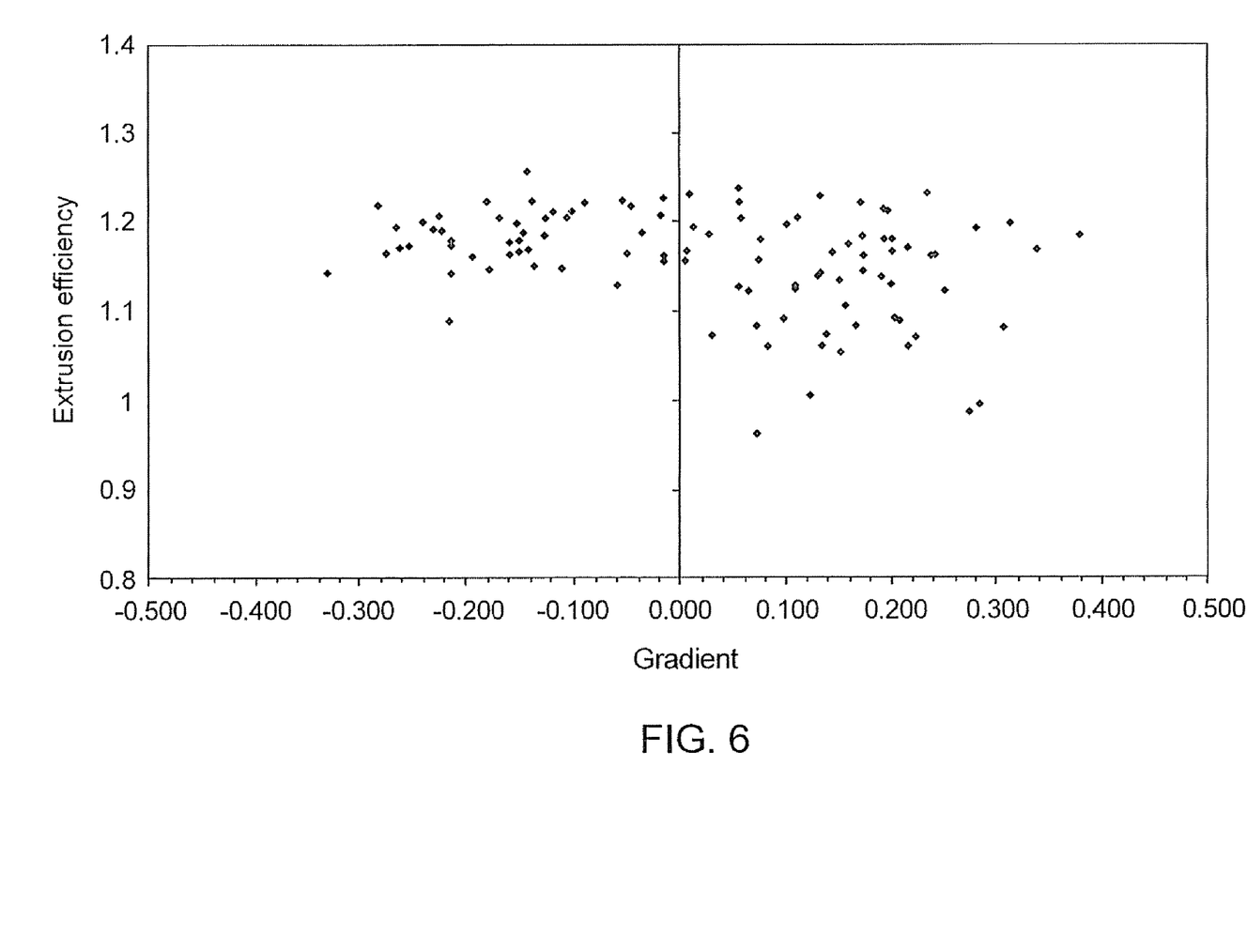
FIG. 6 is a graph that illustrates the extrusion efficiency of the porous sheet with a gradient applied as well as the condition with no gradient.

FIG. 6 is a graph that illustrates the effect of gradient incorporated into the porous sheet on the extrusion efficiency, or stated another way, the aerosol generation efficiency. The graph illustrates the correlation between extrusion efficiency and the amount of gradient present in the porous sheet. Extrusion efficiency is defined as ratio of chemical emitted dose and delta packet weight, where delta packet weight represents the net amount of liquid formulation that is extruded through the porous sheet. Hence, extrusion efficiency is a measure of how effectively the liquid formulation is converted to the delivered dose or aerosol present to the patient.

From FIG. 6, it is apparent that the extrusion efficiency has a higher mean value and a lower standard deviation or variance in the case where the porous sheet exhibits a negative gradient. This higher mean and lower standard deviation translate into improved utilization of a liquid formulation of a pharmaceutically active drug or diagnostic agent. The results also show improved repeatability, i.e. less potential dose-to-dose variation if a porous sheet with negative gradient is employed in the intrapulmonary delivery of said liquid formulations.

It should be noted that the scatter in the points presented in FIG. 5 and FIG. 6 does not represent the normal variance of the process used to form the pores, but rather, these points are discrete conditions that were generated intentionally through manipulation of the excimer laser used to ablate the sheets of material.

Figure 7:
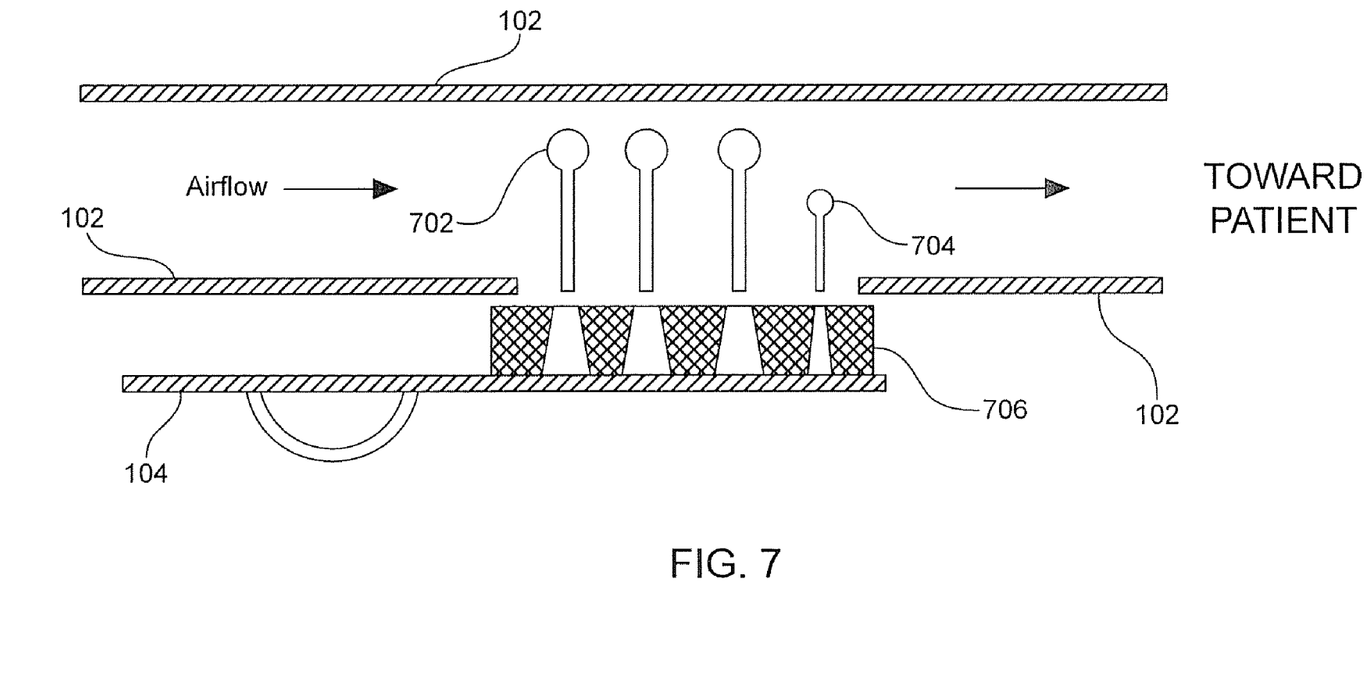
FIG. 7 is a graphical representation of the interaction of the airflow through the device with a porous sheet containing a negative gradient.
Figure 8:
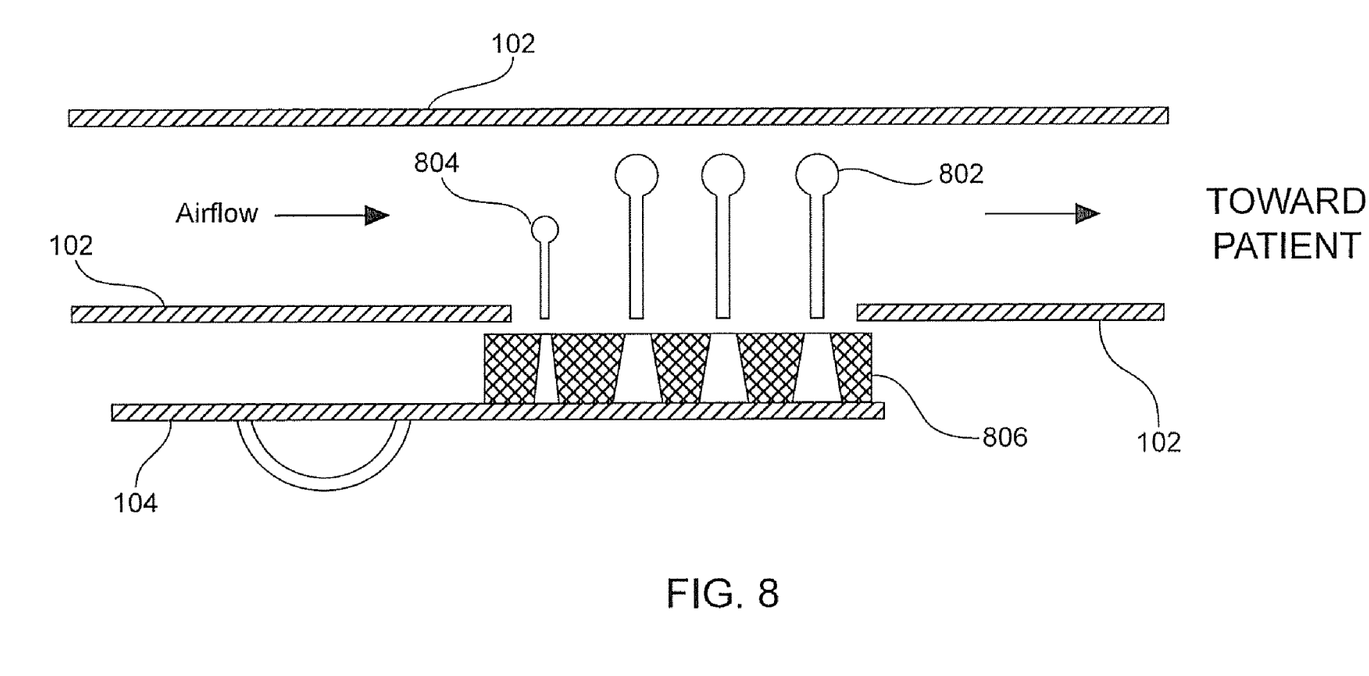
FIG. 8 is a graphical representation of the interaction of the airflow through the device with a porous sheet containing a positive gradient.

FIG. 7 and FIG. 8 illustrate the dynamic condition wherein different pore sizes lead the formation of jets of varying intensity with respect to the velocity and diameter of the jet for a negative gradient and a positive gradient respectively. The characteristics of this jetting will be a function of the pore diameter. In practice, the surface tension of the liquid being extruded causes droplets to form and subsequently break off from these jets during the extrusion of the liquid formulation through the porous sheet. It is these droplets of liquid that form the aerosol that is ultimately delivered to the patient via the intrapulmonary delivery of a pharmaceutically active drug or diagnostic agent. Within FIG. 7 the wider jet 702 of liquid formulation is shown which exits from the larger nozzle hole in the nozzle substrate material 706. The jet 702 is wider than the narrow jet 704 which exits from a smaller opening in the substrate material. In FIG. 8 the wider jet 802 is shown exiting from the wider opening in the substrate material 806. The jet 802 is wider as compared to the narrower jet 804 which exits from the smaller opening in the substrate 806.

Under certain circumstances, particularly, but not limited to the formation of aerosols with a mean particle size in the range of 0.5 microns to 12 microns, there is a risk of the liquid formulation exiting the pore of the porous sheet as a liquid as opposed to being an aerosol and subsequently pooling on the surface of the porous sheet. This phenomenon is called "ooze". Over the course of an extrusion event, i.e. the period over which the liquid formulation is aerosolized through the porous sheet, this ooze can propagate to adjacent pores within the array of pores on the sheet. The impact of ooze on the porous array on the sheet is to effectively quench those pores wherein jetting and subsequent aerosol generation no longer occurs. As a result a significant amount of the loaded dose from the liquid formulation container is not efficiently delivered as an aerosol to the end user.

In the current embodiment of the invention, it has been observed that a gradient and more specifically, a negative gradient is preferred. The negative gradient effectively creates adjacent rows with increasing larger pore sizes that will mitigate the effect of ooze from the adjacent smaller pores in addition to facilitating longer extrusion times before the onset of ooze formation. This improvement in aerosol generation efficiency through the gradient in pore size is realized while still maintaining the particle size distribution in the desired range to ensure effective delivery of the pharmaceutically active drug or diagnostic agent. Additionally, the inclusion of negative gradient to the porous sheet leads to significantly reduced variability in the aerosol generation and performance as observed in the reduced standard deviations, thus facilitating more reliable and consistent dosing to the patient.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims.

Sheet Dimensions and Materials

The sheet materials that can be used for forming pores with a gradient include, but are not limited to flexible and non-flexible sheets, that are either organic or inorganically based. An example of a flexible, organic sheet could include materials such as, but not limited to polycarbonates, polyimides, polyamides, polysulfone, polyolefin, polyurethane, polyethers, polyether imides, polyethylene and polyesters. Co-polymers or shape memory polymers can also be used. Examples of non-flexible, inorganic sheet materials can include, but are not limited to, aluminum, gold, platinum, titanium, nickel, alloys of steel, silicon, silica, glasses, and ceramics.

The thickness of the sheet material has effects on both the manufacturing and configuration of the pore design as it relates to aerosol performance. The sheet is preferably from 10 to about 200 micrometers in thickness, more preferably from 20 to 100 micrometers, and most preferably about 12 to 45 micrometers in thickness. In the preferred embodiment, the thickness is about 25 micrometers.

Pore Sizes and Characteristics

The terms "particle diameter" and "particle size" are used interchangeably herein to refer to the particle size as defined by the aerodynamic size of the particle, where the aerodynamic diameter represents the diameter of a unit density particle having the same terminal sedimentation velocity in air under normal atmospheric conditions.

The sheet as defined in this invention will contain a plurality of pores. In some embodiments of the invention, the sheet will comprise of a plurality of porous areas separated from one another by non-porous areas of the sheet.

The pores on the sheet may be arranged in rectangular arrays, such as in rows and columns or grids of pores at regular, substantially uniform distances from one another. Alternatively, the pores may also be arranged in a circular fashion or some other geometric orientation where the subsequent rows or rings of pores can be described in radial coordinates. Other geometries could also be used, or the pores could be randomly distributed.

The pores formed on the sheet may be cylindrical or conical in shape. In the example of cylindrical pores, the pores pass perpendicularly through the sheet maintaining approximately the same diameters at the entrance and exit sides of the sheet. In the more common application of conical pores, the pores are larger on one side of the sheet and become progressively smaller in diameter on the opposing side of the sheet. The shape of the pore walls can take on either a straight or curved taper in the case of the conical pores. The pores can also have a stepped configuration, wherein the first section of the pore is a relatively large hole, having in its base a smaller cylindrical, or preferably conical pore.

Sheets containing uniform arrays of pores and their formation have previously been described in U.S. Pat. No. 6,732,943. In this embodiment however, an intentional gradient is imparted into the array or plurality of pores. This is non-uniformity in pore size is done to impart measurable improvement in the aerosolization efficiency, particularly over extended extrusion times. In one embodiment of this invention, the pore size ranged from 0.90 microns to 1.20 microns within an array of 7 rows of 64 columns of pores, with two of the rows featuring pores of 0.90 microns and five of the rows featuring pores of 1.20 microns. It is preferred that the gradient lead to a change in hole size from one side of the array to the other of at least 5%, preferably at least 10%, more preferable at least 20%.

Laser Source

The specific laser source used in the method of invention will to some degree be dependent upon the material or sheet in which the pores are to be formed. In general, the laser source should possess sufficient energy at specific wavelengths to effectively ablate material from the sheet in which the pores will be formed. This wavelength is typically in the 150 to 360 nm range.

One laser that has been demonstrated effective for forming the pores with the desired gradient as described in this invention is a frequency tripled neodymium yttrium aluminum garnet (Nd:YAG) laser. This laser is a pulsed laser that can be operated in the ultraviolet wavelength spectrum at a sufficiently high peak power in short pulses to permit the precise ablation of pores in sheets of material. The beam profile for the Nd:YAG laser is radially symmetric which facilitates the formation of radially symmetric pores of well defined and controlled sizes. The Nd:YAG laser can be used to create the desired matrix of pores exhibiting gradient through a number of methods including, but not limited to 1) ablating each pore or collection of pores separately with or without feedback, 2) using a different number of pulses for each pore or collection of pores, 3) using a different power for the ablation of each pore or collection of pores, 4) varying the focus for the ablation of each pore or collection of pores, and 5) creating gradient through the use of a diffractive optic element, wherein the optic element is designed to create the desired level of gradient.

Another laser system that has been demonstrated to be effective in the formation of a plurality of pores exhibiting a gradient in the pore size is the excimer laser system. Like the Nd:YAG laser, the excimer laser is a pulsed laser generating sufficient peak energy in the ultraviolet wavelength spectrum to ablate or dither materials in a sheet form. The excimer laser utilizes a photomask with the desired pore configuration to form the pores on the sheet by projecting the ultraviolet energy through said photomask. This arrangement is capable of simultaneously ablating or dithering one or more conical or cylindrical pores in the sheet material. As the projected beam from the excimer laser is not radially symmetric the desired gradient in pore size can be accomplished either by creating the desired configuration directly using the photomask or by biasing the energy from the laser to create a non-uniform energy field. Alternatively, the projected beam from the excimer laser could be used to create the desired configuration by ablating a gradient in the matrix of pores using either a single photomask or multiple photomasks with the desired features. Alternatively, the focus could be varied across the material to create a gradient.

It will be obvious to one skilled in the art that many other types of LASERs could be used to form the array, including but not limited to Nd:YLF lasers, Argon ion lasers, $CO_2$ lasers, Ruby lasers, He—Ne Laser, Diode lasers, Nd: YAG lasers, Femto-second lasers and Excimer lasers, and the Lasers can be operated at their fundamental wavelength or up converted, including frequency doubled, tripled, or higher harmonics.

It will be obvious to one skilled in the art that many techniques can be used to form the array, including but not limited to Micro-Electro-Mechanical Systems (MEMS), embossing, electric discharge, track etching, molding, and the like.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A drug delivery device, comprising:
   a drug container for holding a liquid formulation; and
   a flexible sheet of material having a nozzle area in fluid connection with the container, the nozzle area having a plurality of pores therein which pores form a population of pores;
   wherein the pores of the population of pores comprise openings on a first side of the sheet and the openings change in opening size in a manner chosen from (a) a continuous and gradual change from a first edge of the sheet to a second edge of the sheet; and (b) a discrete change of pore sizes from the first edge of the sheets to the second edge of the sheet;
   wherein the change in pore size in the population provides a negative gradient, wherein the pore sizes decrease in a direction of airflow.

2. The device of claim 1, wherein the change in opening size from the first edge to the second edge is a change of at least 10% in the hole size in the population of pores.

3. The device of claim 1, wherein the flexible sheet is comprised of a polymer selected from the group consisting of polyamides, polyether imides, polyesters, and polycarbonate.

4. The device of claim 1, wherein an average ratio of entrance pore diameters with respect to an average of the exit pore sizes diameters is a ratio of at least 10:1.

5. The device of claim 1, wherein an average ratio of the entrance pore diameters with respect to an average of the exit pore sizes diameters is a ratio of at least 20:1.

6. The device of claim 1, wherein the sheet of material is comprised of a non-flexible sheet of a material selected from the group consisting of stainless steels, titanium, aluminum, silicon, nickel, glass, or ceramic and wherein the nozzle area with pores therein contains 5 to 5000 pores and wherein the pores are conical.

7. The device of claim 1, wherein the nozzle area contains 100 to 1000 pores.

8. The device of claim 1, wherein the nozzle area contains 300 to 600 pores.

9. The device of claim 1, wherein the pores of a population of pores are regularly or irregularly spaced in the nozzle in rows and columns in a rectangular array.

10. The device of claim 9, wherein the pores in each row are of substantially the same size.

* * * * *

UNITED STATES PATENT AND TRADEMARK OFFICE
CERTIFICATE OF CORRECTION

| | |
|---|---|
| PATENT NO. | : 7,958,887 B2 |
| APPLICATION NO. | : 11/683919 |
| DATED | : June 14, 2011 |
| INVENTOR(S) | : Giles Kelliher et al. |

It is certified that error appears in the above-identified patent and that said Letters Patent is hereby corrected as shown below:

At column 14, claim 4, line 19, please delete the word "sizes"; and

At column 14, claim 5, line 22, please delete the word "sizes".

Signed and Sealed this
Twenty-eighth Day of February, 2012

David J. Kappos
*Director of the United States Patent and Trademark Office*